United States Patent [19]

Kongerslev et al.

[11] Patent Number: 5,356,798
[45] Date of Patent: Oct. 18, 1994

[54] RECOMBINANT PROTEIN PRODUCTION IN SERUM-FREE MEDIUM

[75] Inventors: Leif Kongerslev, Birkerod; John Pedersen, Kokkedal, both of Denmark

[73] Assignee: Novo Nordisk A/S, Bagsvaerd, Denmark

[21] Appl. No.: 48,938

[22] Filed: Apr. 23, 1993

[30] Foreign Application Priority Data

Apr. 24, 1992 [DK] Denmark ............................ 0537/92

[51] Int. Cl.$^5$ .................. C12P 21/06; C12N 5/00; C07K 3/00; A61K 35/14
[52] U.S. Cl. .................. 435/69.6; 435/69.1; 435/240.2; 435/240.3; 435/240.31; 435/320.1; 530/359; 530/383
[58] Field of Search .................. 435/69.6, 69.1, 240.2, 435/240.3, 240.31, 320.1; 530/359, 383

[56] References Cited

U.S. PATENT DOCUMENTS

4,980,456 12/1990 Scandella et al. .................. 530/383

FOREIGN PATENT DOCUMENTS

| | | |
|---|---|---|
| 0055835 | 7/1982 | European Pat. Off. . |
| 0150735 | 8/1985 | European Pat. Off. . |
| 0160457 | 11/1985 | European Pat. Off. . |
| 0232112 | 8/1987 | European Pat. Off. . |
| 0251843 | 1/1988 | European Pat. Off. . |
| 0253455 | 1/1988 | European Pat. Off. . |
| 0254076 | 1/1988 | European Pat. Off. . |
| 0303540 | 2/1988 | European Pat. Off. . |
| 0265778 | 5/1988 | European Pat. Off. . |
| 0294910 | 12/1988 | European Pat. Off. . |
| 0441695 | 8/1991 | European Pat. Off. . |
| 61-63283 | 4/1986 | Japan . |
| WO85/01961 | 5/1985 | PCT Int'l Appl. . |
| WO86/06101 | 10/1986 | PCT Int'l Appl. . |
| WO87/04187 | 7/1987 | PCT Int'l Appl. . |
| WO87/07144 | 12/1987 | PCT Int'l Appl. . |
| WO88/00831 | 2/1988 | PCT Int'l Appl. . |
| WO91/07490 | 5/1991 | PCT Int'l Appl. . |
| WO91/09122 | 6/1993 | PCT Int'l Appl. . |

OTHER PUBLICATIONS

Murakami et al "Egg yolk Lipoprotein . . . " Cytotechnology 1(2) pp. 159–170 1988.
Dialog Info. Svce., Abstract of JP 1235586 (1989).
D. K. Fujii et al., J. of Cellular Physiol., vol. 114, pp. 267–278 (1993).
Dialog Info. Svce., Abstract of JP 1289484 (1989).
Abstract of Yui S. et al., J. Immunol., vol. 136, No. 4, pp. 1334–1338 (1986).
Yau-Young et al., Biochimica et Biophysica Acta, vol. 710, pp. 181–187 (1982).
Dialog Info. Svce., Abstract of Ito H. et al., Nippon Hinyokika Gakkai Zasshi, vol. 80, No. 12, pp. 1741–1748 (1989).
Dialog Info. Svce., Abstract of Martis et al., In Vitro Cell Dev. Biol. vol. 22, No. 5, pp. 241–246 (1986).
Dialog Info. Svce., Abstract of JP 1083100 (1989).

*Primary Examiner*—Robert A. Wax
*Assistant Examiner*—Hyosuk Kim
*Attorney, Agent, or Firm*—Steve T. Zelson; Cheryl H. Agris

[57] ABSTRACT

In a method for effecting an increased expression in serum-free medium of recombinant proteins in a host cell being able to express said protein said host is cultured in a serum-free medium comprising an egg yolk fraction being free of lipoprotein and lipids so as to express said protein. Also the use of an egg yolk fraction being free of lipoprotein and lipids for increasing the expression of recombinant proteins in a host cell being able to express said protein in a serum-free cell growth medium is disclosed.

6 Claims, No Drawings

RECOMBINANT PROTEIN PRODUCTION IN SERUM-FREE MEDIUM

TECHNICAL FIELD

This invention relates to a method for effecting an increased expression of recombinant proteins in serum-free media.

BACKGROUND OF THE INVENTION

A number of proteins having biological activity, e.g. blood coagulation factors such as Factor VII, Factor VIII, Factor IX, Factor X, and Factor XIII, immunoglobulins or serum albumin have traditionally been isolated from body fluids such as serum as their only source. However, as some of the proteins are only present in small amounts, a vast number of donors have to be involved in order to allow isolation of the proteins in industrial scale. This has given rise to increased concern due to the risk of transferring blood borne diseases which together with the limitation on the natural resources has enhanced the search for alternative methods for producing such proteins in industrial scale without such risks.

Hemophilia A is an X-chromosome-linked inherited disease which afflicts 1-2 males per 10,000. The disease is caused by an absence of deficiency of Factor VIII:C. Factor VIII:C is a very large glycoprotein (native $M_r$ 330K–360K), which is present in plasma at extremely low concentrations. It is a necessary element in the proteolytic cascade which converts soluble fibrinogen to insoluble fibrin, forming a clot to prevent blood loss from traumatized tissue. In the bloodstream, it is found in noncovalent association with von Willebrand factor (vWF) which acts as a stabilizing carrier protein. Factor VIII:C is very susceptible to cleavage by thrombin, plasmin, activated protein C, and other serine proteases. It is generally isolated from plasma or plasma products as a series of related polypeptides ranging from $M_r$ 160K–40K with predominant species of $M_r$ 92K and $M_r$ 80K–77K. This complex pattern has made the analysis of the structure of active Factor VIII:C very difficult.

Recombinant proteins produced according to the invention may be Factor VII, Factor VIII, Factor IX, Factor X, and Factor XIII which may be used for substitution therapy in individuals having deficiencies in the coagulation cascade, immunoglobulin which may be used for treating infectious diseases or serum albumin which may be used as substitute for blood transfusion during operations or a constituent of a culture medium.

Recombinant proteins having Factor VIII:C activity being prepared according to the present invention may be full length Factor VIII:C corresponding to the protein isolated from plasma, or a derivative thereof having the capability of normalizing the insufficient blood clotting caused by deficiency of Factor VIII:C. The derivatives of Factor VIII:C may be shortened single chain forms or derivatives comprising two chains. Even fragments of Factor VIII:C which may not per se show coagulant activity, but which may be used in the treatment of hemophiliacs e.g. for saturation of antibodies against Factor VIII:C present in inhibitor patients.

The proteins produced in accordance with the present invention show homology with all or a part of the natural Factor VIII:C molecule.

The preparation of recombinant proteins having Factor VIII:C activity by recombinant techniques has inter alia been disclosed in a number of patent publications.

Thus, European Patent Application No. 160 457 and International Patent Application No. WO 86/01961 disclose the production of full length Factor VIII:C, and European Patent Application No. EP 150 735, International Patent Application No. WO 86/06101, European Patent Application No. EP 232 112, International Patent Application No. WO 87/04187, International Patent Application No. WO 87/07144, International Patent Application No. WO 88/00381, European Patent Application No. EP 251 843, European Patent Application No. EP 253 455, European Patent Application No. EP 254 076, U.S. Pat. No. 4,980,456, European Patent Application No. EP 294 910, European Patent Application No. EP 265 778, European Patent Application No. EP 303 540, International Patent Application No. WO 91/07490, and International Patent Application No. WO 91/09122 disclose recombinant expression of subunits of Factor VIII:C or co-expression of subunits for the production of complexes showing coagulant activity or binding affinity to antibodies inhibiting Factor VIII:C.

Expression of recombinant full length human Factor VIII:C is usually low and the molecule is unstable due to proteolysis.

Derivatives of Factor VIII:C in the form of shortened single chain forms or derivatives comprising two chains have also been successfully produced by recombinant techniques. Although these derivatives normally are expressed in a higher yield than full-length Factor VIII:C, there is still a desire for increasing the level of expression.

In order to obtain an acceptable level of expression and an acceptable stability of a produced recombinant protein having biological activity it is often preferred to express the proteins in mammalian cells. These cells are usually grown in media containing mammalian serum e.g. new borne or fetal bovine serum, in amounts of about 10% serum by volume relative to total media volume. The recombinant protein is secreted into the culture medium and has to be separated from the serum components during the isolation.

However, serum has high contents of proteins which renders the recovery and purification of the desired proteins troublesome. Such addition may also introduce a potential risk of introducing malign viruses from the bovine serum into the final blood preparations. Hence, there is a need to find serum-free culture media or media having reduced amounts of serum for culturing the host cells without essentially reducing the expression or the stability of the desired protein.

Several methods of expressing proteins having biological activity in serum-free media has already been proposed.

WO 87/04187 and EP 251 843 disclose that expression of Factor VIII:C in serum-free medium in the presence of von Willebrand Factor (vWF) or phospholipid increases the expression of Factor VIII:C. In EP 254076 it is disclosed that addition of lipoprotein to a serum-free medium increases the expression of Factor VIII in a host cell carrying the gene encoding Factor VIII. JP 61 063283 discloses that expression of i.a. monoclonal antibodies in serum-free media may be increased by addition of lipoprotein in the form of an egg yolk fraction. Finally, EP 441 695 discloses the expression of Factor VIII:C or an analogue thereof in serum-free medium in the presence of a cationic or anionic polymer, preferably a polysaccharide which most preferred is in a sulphatized form. It has been proposed to accelerate the growth of Myobacterium cultures or to stabilize media for cultivating tuberculosis bacilli by adding whole egg yolk.

The present invention is based on the surprising finding that a fraction of egg yolk not being freed from lipids may be used for increasing the expression of recombinant proteins having biological activity, preferably Factor VIII:C, in serum-free media.

DISCLOSURE OF THE INVENTION

The present invention relates to a method for effecting an increased expression, in serum-free medium, of recombinant proteins in a mammalian host cell being able to express said protein comprising culturing said host in a serum-free growth medium comprising an egg yolk fraction being free of lipoprotein and lipids so as to express said protein.

DETAILED DESCRIPTION OF THE INVENTION

It has surprisingly been found that the addition of an egg yolk fraction being free of lipoprotein and lipids increases the expression, in serum-free medium, of recombinant proteins.

The fraction of egg yolk used according to the invention may be produced by adding polyethylene glycol to a concentration of 3.5% and buffer to egg yolk and stir and centrifuge as disclosed in Immunological Communications, 9(5), 475–493 (1980). In this precipitation, the lipoprotein fraction of the egg yolk is precipitated. The lipoproteins are micelles comprising lipids having their lipophil parts internally and a surface comprising i.a. apoproteins. The lipids are constituted by fatty acids phospholipids and cholesterol. The fraction to be used in accordance with the present invention is the supernatant from the first centrifugation not being a desired fraction according to the above reference dealing with the isolation of antibodies from the precipitate. There is no indication of any use of this supernatant in the reference.

In such separation, all constituents of the lipoproteins which have previously been proposed as supplement to increase the expression of recombinant proteins in serum-free media are isolated from the egg yolk, as a precipitate.

According to a preferred aspect of the invention, the egg yolk fraction is added to a concentration of from 0.5 to 15%, a concentration of from 1 to 10% being more preferred an a concentration of 5 to 10% being most preferred.

According to preferred aspect, the invention relates to a method for effecting an increased expression of a protein having Factor VIII:C activity. According to a more preferred aspect of the invention, the method is used for expression of a complex of the 92 kD and 80/77 kD subunits of Factor VIII:C. For such cultivation the egg yolk fraction does not only increase the level of expression of the individual subunits of Factor VIII:C, but also increases the degree of complex formation and stabilizes the produced complex and thus increases the yield of active product.

In another aspect, the invention relates to the use of an egg yolk fraction being free of lipoprotein and lipids for increasing the expression of recombinant proteins in a host cell being able to express said protein comprising culturing said host in a serum-free cell growth medium.

In still another aspect, the invention relates to the use of an egg yolk fraction being free of lipoprotein and lipids for increasing the expression of recombinant proteins having Factor VIII:C activity.

The term "Heavy Chain (HC)" is used to designate the 92 kD subunit of Factor VIII:C.

The term "Light Chain (LC)" is used to designate the 77/80 kD subunit of Factor VIII:C.

The term "co-expressing" as used herein in combination with proteins having Factor VIII:C activity refers to simultaneous expression of the 92 kD and the 80 kD subunits of Factor VIII:C within the same host cell. The polynucleotide sequences encoding the 92 kD and 80 kD subunits may be on the same or on different expression cassettes or plasmids. Co-expression of the 92 kD and 80 kD subunits permits proper folding to occur, which in turn provides a complex having activity and efficiency of secretion.

The term "cell growth medium" as used herein refers to any medium suitable for culturing host cells, and includes media suitable for obtaining expression of recombinant products whether actual cell "growth" occurs or not. Cell growth media generally include nutrients and a metabolizable energy source in an aqueous solution. If desired, cell growth media may also include a compound which induces expression of the recombinant polypeptides of the invention. Selection of such an inducing compound depends upon the promoter selected to control expression. Other typical additives include selection compounds (i.e., drugs or other chemicals added to the media to insure that only transformed host cells survive in the medium).

The term "serum-free medium" as used herein is intended to designate a solution which has been supplemented to such an extent that the necessary trace factors present in serum need not be added in the form of serum. There are many suitable cell growth media available from commercial sources.

The term "egg extract" is used here to designate a fraction of egg yolk being free of lipoprotein and lipids prepared as described in Immunological Communications (ibid).

The structural genes typically include a leader sequence coding for the signal peptide which directs the polypeptide into the lumen of the endoplasmic reticulum for processing and maturation. Optionally included are additional sequences encoding propeptides which are processed post-translationally by endopeptidases, where the endopeptidases cleave a peptide bond, removing the propeptide to generate the mature polypeptide. The signal peptide may be the naturally occurring one, particularly for the N-terminal peptide, or may be any signal peptide which provides for the processing and maturation of the polypeptides.

Various mammalian host cells may be employed in which the regulatory sequences and replication system are functional. Such cells include COS7 cells, Chinese hamster ovary (CHO) cells, mouse kidney cells, hamster kidney cells, HeLa cells, HepG2 cells, or the like, e.g VERO cells, W-138 or MDCK cell lines.

Proteins having Factor VIII:C activity produced according to the invention are primarily intended for treatment of hemophiliacs and patients suffering from other conditions involving blood clotting disorders. The subject proteins may be administered in physiologically acceptable carrier, such as water, saline, phosphate buffered saline, and citrate buffered saline, at concentrations in the range of about 10–200 U/mL. See U.S. Pat. Nos. 3,631,018; 3,652,530, and 4,069,216 for methods of administration and amounts. Other conventional additives may also be included. They also have a variety of uses as immunogens for the production of antibodies, for isolation of von Willebrand factor by affinity chromatography and in diagnostic assays for Factor VIII:C.

The invention is explained more in detail in the below examples which provide guidance to the skilled art worker how to work the invention and are not to construed as limiting the scope of protection.

EXPERIMENTAL PART

Materials and Methods

The cell growth medium used was prepared as follows: Seromed mem-Dulbeco TZ 043C powder for 10 l was dissolved in 8.5 l Milli-Q-water.

The following was then added:
0.977 g $MgSO_4$ anhydrous
37.0 g $NaHCO_3$
6.2 g NaCl
1.5 g l-proline
1.1 g Na-pyruvate After adjusting the pH to 7.4 using hydrochloric acid the volume was adjusted to 9 l by adding demineralized water.

The solution was sterile filtered.

When used, 10% 1M aqueous NaCl was added.

A basis medium was then prepared by adding the following constituents:

2.5 g/l Papain digested soy protein
5 mg/l insulin
5.5 mM Gly-Gly
25 $\mu$M $Fe_2(SO_4)_3$
6.5 $\mu$g/l Sodium selenite
0.1 g/l Dextran MW 67000
0.5 g/l $\epsilon$-ACA

EXAMPLE 1

Providing Cell Lines Co-Expressing Factor VII:C Heavy Chain and Light Chain

Transfection-procedure

The DHFR− CHO cell line DG44 (G. Urlaub et al., Som Cell Mol Genet (1986) 12:555–566) was first transfected with the plasmid pCMF8-80AT: In this plasmid the CMV promoter (described in example 7 of WO 91/07490) transcribes the FVIII-LC cDNA derived from pSVF8-80AT (described in example 6) and downstream is placed the Ad-MLP/dhfr casette derived from pad-DHFR (described in example 4 of WO 91/07490). The transfection method used was the polybrene method of W. Chaney et al. (Som Cell Mol Genet (1986) 12:237–244). By selection of DHFR+ cells (DMEM+10% DFCS) several FVIII-LC producers were isolated; one of these was designated 11W.

In order to introduce FVIII-HC in 11W the cell line was cotransfected with the plasmid pPR78 (this plasmid is an analog to pCMVF8-80AT, but harbors instead of the FVIII-LC cDNA the FVIII-HC cDNA derived from pCMVF8-92R described in example 8 of WO 91/07490) and pSV2-neo (P. J. Southern and P. Berg, J Mol Appl Genet (1982) 1:327–341). The transfection method used was the modified calcium phosphate procedure of C. Chen and H. Okayama (Mol Cell Biol (1987) 7:2745–2752). Transfectants were isolated in medium containing 700 $\mu$g Geneticin (G418 Sulphate, Gibco) per ml. Cells from the primary pool were subcloned by the limited dilution method and the individual clones were tested for expression of active FVIII. In this way several FVIII:C producing cell lines were isolated and one of these was designated "45".

The cells selected in this way on the basis of the expression level were seeded into T-flasks for cultivation in the absence of egg extract or in the presence of egg extract in various concentrations.

The description of transfection referred to in WO 91/07490 is hereby incorporated by reference, including the reference to the plasmids pSVF8-92, pSVF8-80 and pSVF8-200 deposited under the accession number ATCC 40222, ATCC 40223 and ATCC 40190, respectively.

EXAMPLE 2

Culturing Cell Line Co-Expressing Factor VIII:C Heavy Chain and Light Chain

The results of cultivating in T-flasks as described above, are shown in the below Tables.

The following additions of egg extract were tested: 1%, 2.5%, 5% and 10% in basis medium. These were compared with the basis medium without addition of egg extract.

In Table 1 is stated the result of the determination of coagulant activity by Coatest kit (KabiVitrum), and in Table 2 and 3 the results of the determination of FVIII:HC and FVIII:LC, respectively.

TABLE 1

| | FVIII:C U/ML | | | | |
| DAYS | 1 BASIS + 10% egg extr. | 2 BASIS + 5% egg extr. | 3 BASIS + 2.5% egg extr. | 4 BASIS + 1% egg extr. | 5 BASIS |
| --- | --- | --- | --- | --- | --- |
| 3 | 1.120 | 0.58 | 0.549 | 0.47 | 0.310 |
| 5 | 2.778 | 1.48 | 1.300 | 0.97 | 0.725 |
| 7 | 3.947 | 2.77 | 2.280 | 1.99 | 1.470 |
| 10 | 8.440 | 5.44 | 4.430 | 4.08 | 2.920 |

TABLE 2

| | FVIII:HC U/ML | | | | |
| DAYS | 1 BASIS + 10% egg extr. | 2 BASIS + 5% egg extr. | 3 BASIS + 2.5% egg extr. | 4 BASIS + 1% egg extr. | 5 BASIS |
| --- | --- | --- | --- | --- | --- |
| 3 | 5.25 | 3.90 | 2.95 | 3.05 | 2.25 |
| 5 | 12.65 | 7.60 | 6.90 | 7.05 | 7.10 |
| 7 | 24.50 | 17.35 | 14.00 | 14.80 | 13.80 |
| 10 | <50 | 44.00 | 38.50 | 39.00 | 35.00 |

TABLE 3

| | FVIII:LC U/ML | | | | |
| DAYS | 1 BASIS + 10% egg extr. | 2 BASIS + 5% egg extr. | 3 BASIS + 2.5% egg extr. | 4 BASIS + 1% egg extr. | 5 BASIS |
| --- | --- | --- | --- | --- | --- |
| 3 | 18.10 | 13.6 | 14.0 | 13.87 | 12.60 |
| 5 | 34.50 | 22.0 | 25.0 | 25.57 | 22.25 |
| 7 | 49.00 | 38.5 | 33.5 | 32.09 | 32.50 |
| 10 | 109.50 | 99.5 | 79.5 | 68.08 | 62.00 |

What is claimed is:

1. In a method of making recombinant blood coagulation factors expressed in a mammalian host cell cultured in a serum-free medium, wherein the improvement comprises adding an egg yolk fraction free of lipoprotein and lipids to the serum-free medium.

2. The method according to claim 1, wherein the concentration of the egg yolk fraction is from 1 to 15%.

3. The method according to claim 1, wherein the concentration of the egg yolk fraction is from 1 to 10%.

4. The method according to claim 1, wherein the concentration of the egg yolk fraction is from 1 to 5%.

5. The method according to claim 1, wherein the recombinant blood coagulation factor is a protein having Factor VIII:C activity.

6. The method according to claim 5, wherein the protein having Factor VIII:C activity is a complex of the 92 kD and 80/77 kD subunits of Factor VIII:C.

* * * * *